US009801657B2

(12) United States Patent
Furnish et al.

(10) Patent No.: US 9,801,657 B2
(45) Date of Patent: Oct. 31, 2017

(54) EXPANDABLE INTRODUCER SHEATH (71) Applicant: Freudenberg Medical, LLC, Carpinteria, CA (US)

(72) Inventors: Simon Furnish, Louisville, KY (US); Anthony Appling, Crestwood, KY (US)

(73) Assignee: FREUDENBERG MEDICAL, LLC, Carpinteria, CA (US)

( * ) Notice: Subject to any disclaimer, the term of this patent is extended or adjusted under 35 U.S.C. 154(b) by 404 days.

(21) Appl. No.: 14/484,887

(22) Filed: Sep. 12, 2014

(65) Prior Publication Data
US 2016/0074067 A1   Mar. 17, 2016

(51) Int. Cl.
*A61B 17/34* (2006.01)
*A61M 25/00* (2006.01)
*A61M 25/06* (2006.01)
*A61B 17/00* (2006.01)

(52) U.S. Cl.
CPC ...... *A61B 17/3439* (2013.01); *A61B 17/3415* (2013.01); *A61B 17/3468* (2013.01); *A61M 25/005* (2013.01); *A61M 25/0023* (2013.01); *A61M 25/0052* (2013.01); *A61M 25/0662* (2013.01); *A61B 17/3431* (2013.01); *A61B 2017/00853* (2013.01); *A61B 2017/00955* (2013.01); *A61M 2025/0024* (2013.01); *A61M 2205/0222* (2013.01)

(58) Field of Classification Search
CPC ............ A61B 17/3439; A61B 17/3468; A61B 17/3415; A61B 2017/00853; A61M 25/0052; A61M 2205/0222
USPC ........ 600/37; 604/101.1, 103.6, 131, 164.03, 604/164.08, 167.01, 167.03, 284, 43, 507, 604/508, 509, 523, 526, 528; 606/108, 606/159, 194, 195, 198, 200; 623/1.11, 623/1.12, 1.13, 1.15, 1.22, 2.11
See application file for complete search history.

(56) References Cited

U.S. PATENT DOCUMENTS

| | | | |
|---|---|---|---|
| 4,921,479 | A | 5/1990 | Grayzel |
| 5,256,150 | A | 10/1993 | Quiachon et al. |
| 5,935,122 | A | 8/1999 | Fourkas et al. |
| 5,997,508 | A | 12/1999 | Lunn et al. |
| 6,183,443 | B1 | 2/2001 | Kratoska et al. |

(Continued)

FOREIGN PATENT DOCUMENTS

WO   WO2014066031 A1   5/2014

OTHER PUBLICATIONS

Search Report dated Sep. 28, 2015 in corresponding European Patent Application No. 15182410.9.

*Primary Examiner* — Vy Bui
(74) *Attorney, Agent, or Firm* — Dickinson Wright PLLC (57) ABSTRACT An expandable introducer sheath for use in inserting a medical device into a body vessel of a patient includes a body which extends from a proximal end to a distal end along an axis. The body includes an inner layer, an outer layer, and an expandable reinforcement member which is disposed between said inner and outer layers. The expandable reinforcement member is configured to radially expand as the medical device is axially advanced or retracted through said introducer sheath. Once the medical device has exited the introducer sheath, the expandable reinforcement member facilitates a return of the introducer sheath to its original or unexpanded condition.

19 Claims, 6 Drawing Sheets

(56) References Cited

U.S. PATENT DOCUMENTS

| | | |
|---|---|---|
| 6,443,979 B1 | 9/2002 | Stalker et al. |
| 7,713,281 B2 * | 5/2010 | Leeflang ............ A61B 17/3439 606/194 |
| 9,192,751 B2 * | 11/2015 | Macaulay ......... A61M 25/0023 |
| 2005/0085841 A1 | 4/2005 | Eversull et al. |
| 2008/0004571 A1 | 1/2008 | Voss |
| 2008/0188928 A1 | 8/2008 | Salahieh et al. |
| 2009/0240202 A1 | 9/2009 | Drasler et al. |
| 2010/0082000 A1 | 4/2010 | Honeck et al. |
| 2010/0094392 A1 * | 4/2010 | Nguyen ................ A61F 2/2427 623/1.11 |

\* cited by examiner

EXPANDABLE INTRODUCER SHEATH

BACKGROUND OF THE INVENTION

1. Field of the Invention

The present disclosure relates generally to medical devices and procedures. In particular, the present disclosure relates to expandable medical devices, such as introducer sheaths, for use during medical procedures.

2. Description of the Prior Art

This section provides background information related to the present disclosure which is not necessarily prior art.

Numerous procedures have been developed that involve the percutaneous insertion of a medical device into the body of a patient, with the medical device being introduced into the body by a variety of known techniques. For example, access to coronary arteries, carotid arteries, the aorta, and peripheral vessels or other tubular members of the body for percutaneous therapeutic, diagnostic, and guide catheters is often made through introducer sheaths which are positioned into body vessels from outside the bodies. Such access sites include, but are not limited to, the common femoral artery/vein and the radial arteries, as well as the ureter, urethra, intestinal track, veins and other tubular tissues. However, the use of introducer sheaths and/or medical devices which are large relative to the body vessels to which they are inserted poses risks and challenges to both the patient and the physician.

For example, relative to femoral sheaths and catheters, larger introducer sheaths create sizeable arteriotomies in the femoral artery which cause more trauma to the patient, such as through artery avulsion, and create more challenges in placement of the sheath with risk of dissection. In addition, the forces required by the physician to insert the larger introducer sheaths and/or medical devices into the body vessel can be higher than desired and create medical issues for the patient if calcification within the body vessel is dislodged during insertion of the introducer sheath and/or medical device.

Methods of accessing a body vessel with a larger introducer sheath and/or medical device can begin by dilating the vessel with a radially expanding intravascular sheath assembly prior to introducing the medical device. However, such radially expanding sheaths have complex mechanisms, such as ratcheting or balloon mechanisms, that expand and maintain the sheath in an expanded configuration while a medical device with a large diameter is introduced. Further, since the mechanisms effectuate the expansion of the body vessel, they do not provide a user with tactile feedback, and can even pose a risk of dissection during the procedure. Accessing the body vessel remains a challenge with existing expandable sheath assemblies due to the relatively large profile of the medical device inserted which causes longitudinal and radial tearing of the vessel during insertion. As mentioned above, these prior art delivery systems can even dislodge calcified plaque within the vessels during insertion, posing an additional risk of clots caused by the dislodged plague.

Accordingly, there remains a need in the art for an improved expandable introducer sheath for use with the percutaneous insertion of a medical device into a body vessel of a patient.

SUMMARY OF THE DISCLOSURE

This section provides a general summary of the disclosure and is not intended to be a comprehensive disclosure of its full scope, aspects, objectives, and/or all of its features.

An expandable introducer sheath for use in inserting a medical device into a body vessel of a patient includes a body extending from a proximal end to a distal end along an axis. The expandable introducer sheath includes an inner layer, an outer layer, and an expandable reinforcement member disposed between the inner and outer layers. The expandable reinforcement member is configured to allow for temporary radial expansion of the introducer sheath as a medical device is axially advanced or retracted through the introducer sheath. Once the medical device has exited the introducer sheath, the expandable reinforcement member retracts to its original or static diameter.

When the introducer sheath is disposed within the body vessel, the radially expansion of the expandable reinforcement member effectuates a lifting, and thus an expansion, of the body vessel. As a result, the expandable reinforcement member allows a medical device which has a larger diameter to be axially advanced through the introducer sheath and into the body vessel. The lifting of the body vessel by way of the expandable reinforcement member avoids the need to push the larger medical device past any calcification that is present within the body vessel, and thus reduces trauma to the body vessel. The radially expandable reinforcement member also provides tactile feedback to a user while serially advancing the medical device through the introducer sheath and into the body vessel.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments, and are not all possible implementations and thus are not intended to limit the scope of the present disclosure.

DESCRIPTION OF THE ENABLING EMBODIMENTS

Example embodiments will now be described more fully with reference to the accompanying drawings. The example embodiments are provided so that this disclosure will be thorough and fully convey the scope to those skilled in the art. Numerous specific details are set forth such as examples of specific components, devices, mechanisms, assemblies, and methods to provide a thorough understanding of various embodiments of the present disclosure. It will be apparent to those skilled in the art that specific details need not be employed, that example embodiments may be embodied in many different forms, and that neither should be construed to limit the scope of the disclosure. With this in mind, the present disclosure is generally directed to expandable introducer sheaths of the type used to introduce and withdrawal a medical device (i.e., catheter systems, implants, etc.) into a body vessel of a patient.

Figure 1:
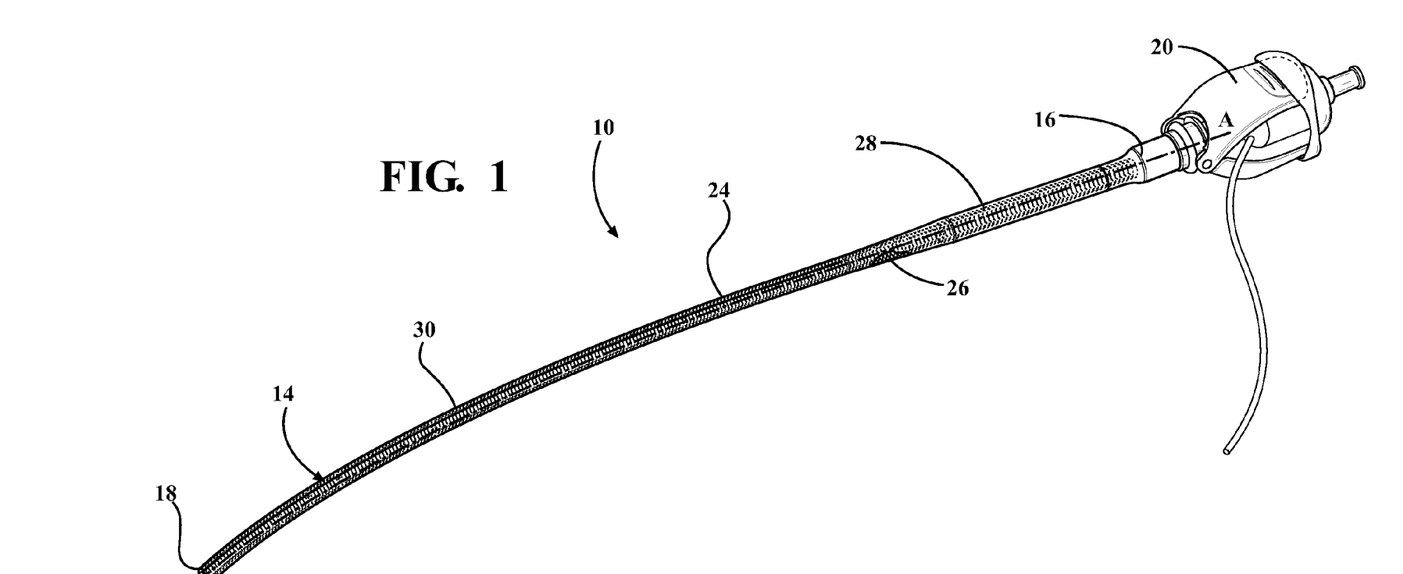
FIG. 1 is a perspective view of an expandable introducer sheath connected to a hemostatic valve assembly and illustrating an outer layer of the expandable introducer sheath.

Referring to the Figures, wherein like numerals indicate corresponding parts throughout the several views, an expandable introducer sheath 10 for use in inserting a medical device 12 into a body vessel of a patient includes a body 14 extending from a proximal end 16 to a distal end 18 along an axis A. As best shown in FIG. 1, in a preferred embodiment, the expandable introducer sheath 10 is secured to a hemostatic valve assembly 20 about the proximal end 16 to dispose the introducer sheath 10 in surrounding and sealed relationship with a passageway of the hemostatic valve assembly 20. Such an arrangement allows the medical device 12 to serially advance along the axis A in sealed relationship from the hemostatic valve assembly 20 to the introducer sheath 10. In a preferred embodiment, the hemostatic valve assembly 20 can be a variable diameter seal hemostatic valve as described in co-owned U.S. patent application Ser. No. 14/326,593 entitled "A Medical Valve with a Variable Diameter Seal", the entire disclosure of which is incorporated by reference. However, other valves, such as iris valves, laparoscopic ports, slit valves, or the like, can also be utilized without departing from the scope of the subject disclosure.

Figure 7A:
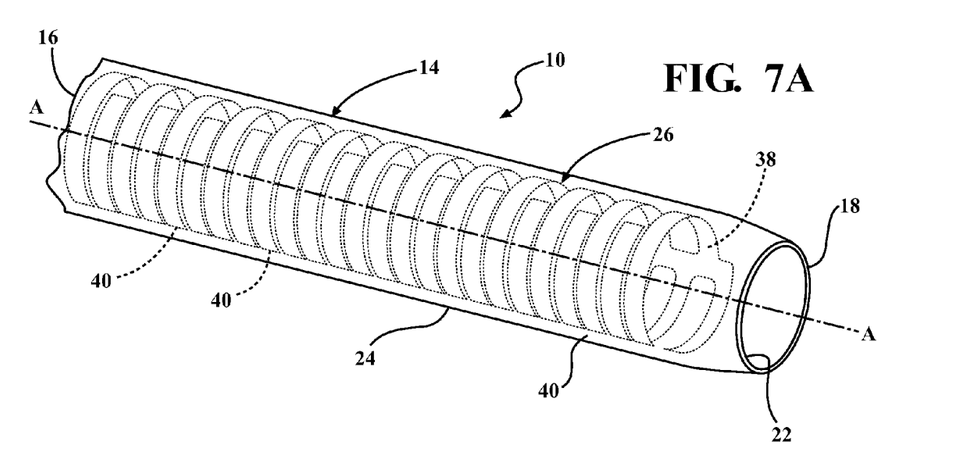
FIG. 7A is a perspective view of the introducer sheath illustrating a first embodiment of an expandable reinforcement member.

As best shown in FIG. 7A, the expandable introducer sheath 10 includes an inner layer 22, an outer layer 24, and an expandable reinforcement member 26 disposed between and surrounded by the inner and outer layers 22, 24. The expandable reinforcement member 26 is comprised of a shape memory material and is configured to allow for temporary radial expansion relative to the axis A of the introducer sheath 10 from an original or static diameter to an expanded diameter as a medical device 12 is axially advanced or retracted through the introducer sheath 10. Once the medical device 12 has exited the introducer sheath 10, the shape memory material of the expandable reinforcement member 26 facilitates a return of the introducer sheath 10 to its original or static diameter. In a preferred arrangement, the shape memory material is a metal alloy such as Nitinol, stainless steel, or the like. However, the shape memory material could also comprise a rigid thermoplastic material conducive to the above-described function without departing from the scope of the subject disclosure.

The expanding or contracting of the expandable reinforcement member 26 effectuates a corresponding radial expansion or contraction of the outer layer 24. When the introducer sheath 10 is disposed within the body vessel, the radial expansion of the outer layer 24 effectuates a lifting, and thus an expansion, of the body vessel to allow a larger medical device 12 to be advanced into the body vessel. The lifting of the body vessel by way of the outer layer 24 of the introducer sheath 10 avoids the need to push the larger medical device 12 past any calcification that is present within the body vessel, and thus reduces trauma to the body vessel. The radial expansion of the outer layer 24 by way of the expandable reinforcement member 26 also provides tactile feedback to a user during serial advancement of the medical device 12 through the introducer sheath 10 and into the body vessel.

Figure 3:
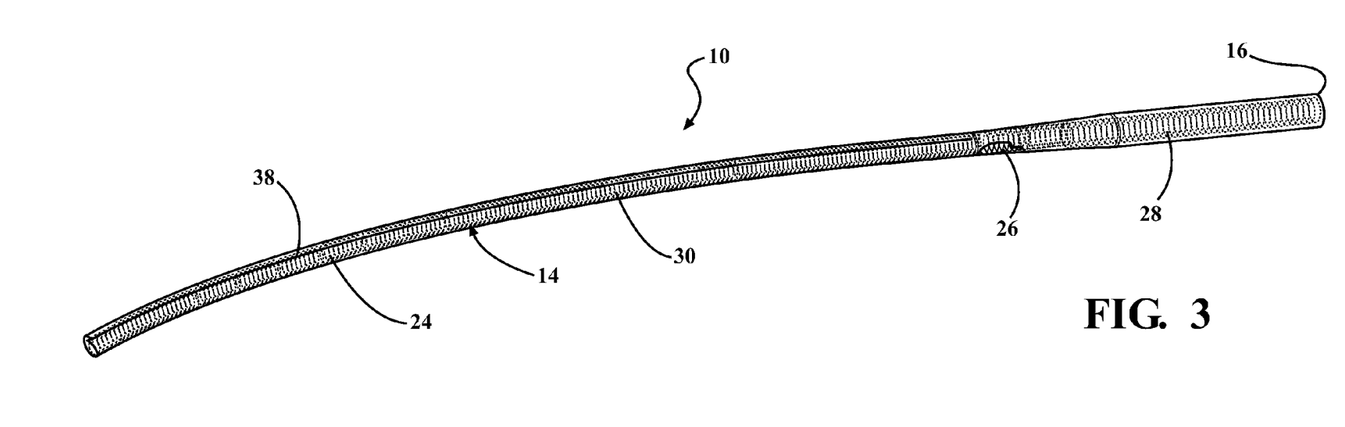
FIG. 3 is a perspective view of the expandable introducer sheath illustrating a longitudinal slit extending along a portion of an outer layer of the introducer sheath.

As best shown in FIGS. 1 and 3, in a preferred arrangement, the body 14 of the expandable introducer sheath 10 includes an enlarged portion 28 disposed adjacent the proximal end 16. The enlarged portion 28 has a first diameter that is sized complementarily to the medical device 12 that will be serially advanced along the axis A though the hemostatic valve assembly 20, the introducer sheath 10 and the body vessel. In this arrangement, the body 14 of the expandable introducer sheath 10 also includes a tapered portion 30 which extends from the distal end 18 to the enlarged portion 28. The tapered portion 30 has a second diameter smaller than the first diameter for providing a smaller profile of the introducer sheath 10 that facilitates an initial insertion of the introducer sheath 10 into the body vessel. Put another way, the tapered portion 30 of the body 14 accommodates an initial insertion of the introducer sheath 10 into the body vessel. By way of the enlarged and tapered portions 28, 30, the body of the introducer sheath 10 can have an original or static outer diameter which decreases or is tapered from the proximal end 16 to the distal end 18. However, it should be appreciated that the body 14 of the introducer sheath 10 can also be designed without the enlarged and tapered portions 28, 30 and thus have an original or static outer diameter which is substantially constant between the proximal and distal ends 16, 18.

Figure 4:
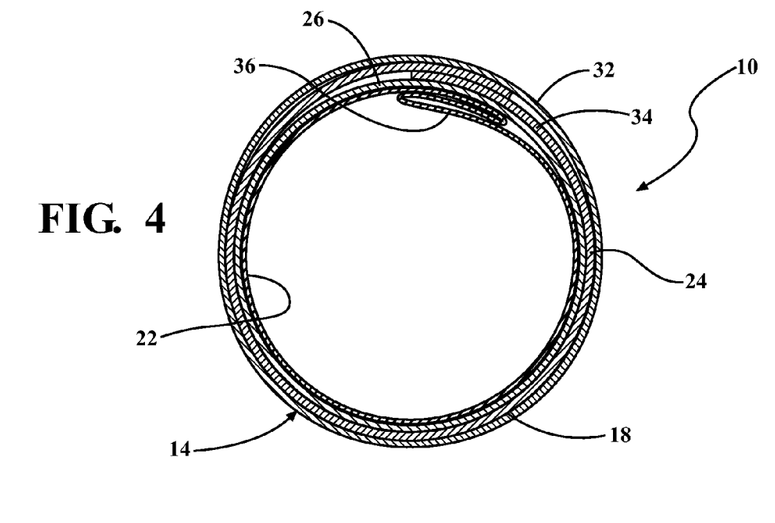
FIG. 4 is an end view of the expandable introducer sheath illustrating a fold in an inner liner of the introducer sheath.
Figure 5:
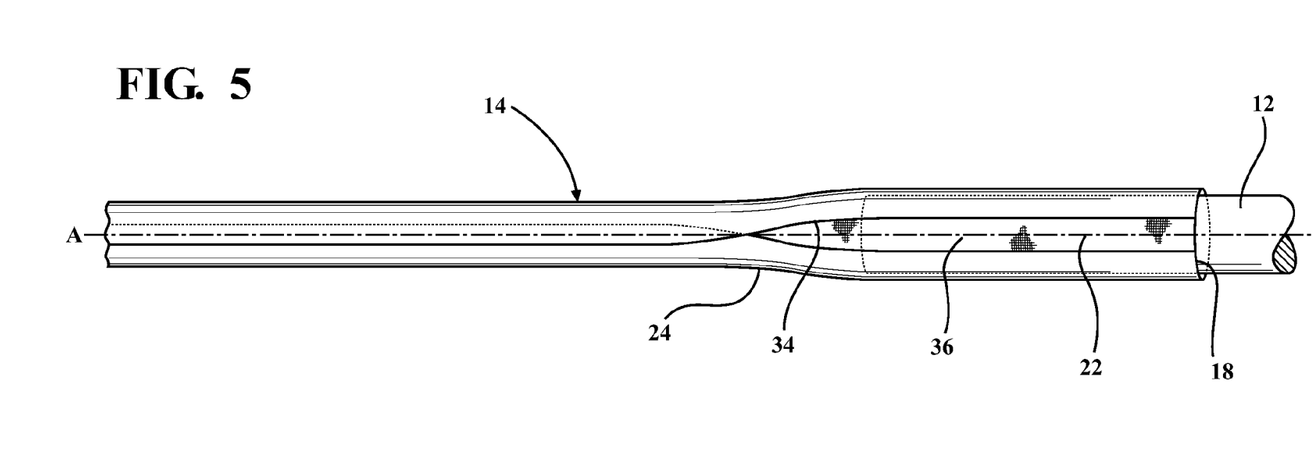
FIG. 5 is a top view of the expandable introducer sheath illustrating the longitudinal slit in a radially expanded condition.
Figure 6:
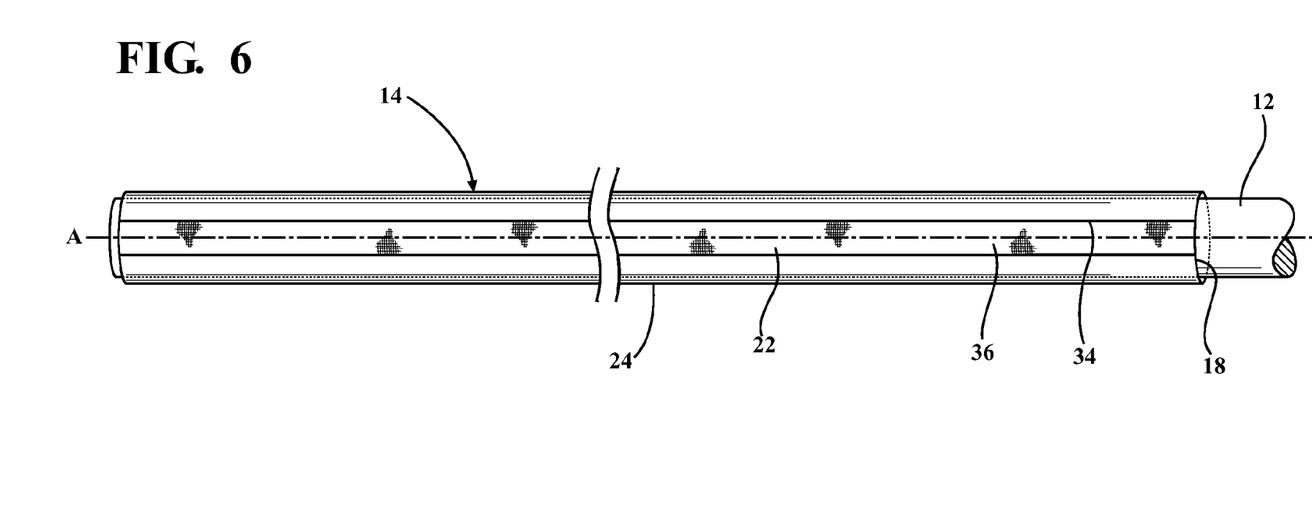
FIG. 6 is a top view of the expandable introducer sheath illustrating the longitudinal slit in a radially expanded condition.

As best shown in FIG. 4, the body 12 of the expandable introducer sheath 10 includes an inner layer 22 which is disposed radially inward of the expandable reinforcement member 26 and which extends between the proximal and distal ends 16, 18. The inner layer 22 is comprised of a lubricious, low friction polymeric material for easing axially movement of the medical device 12 through the expandable introducer sheath 10, and thus easing insertion of the medical device 12 into the body vessel of the patient. By way of example, the inner layer 22 can comprise polytetratluoroethylene (PTFE), polyimide, polyetheretherketone (PEEK), polyurethane, nylon, polyethylene, polyamide, or the like. However, in a preferred embodiment, the low friction polymeric material of the inner layer is comprised of expandable polytetrafluoroethylene (ePTFE).

As best shown in FIGS. 1 and 3, the body 12 of the expandable sheath assembly 10 also includes an outer layer 24 which is disposed radially outward of the expandable reinforcement member 26 and which overlays or surrounds the expandable reinforcement member 26 between the proximal and distal ends 18. In a preferred embodiment, the outer layer is comprised of a thermoplastic material, such as Pevax® (i.e., polyether block amide) or the like. However, an elastomeric material, such as PTFE, polyimide, PEEK, polyurethane, nylon, polyethylene, polyamide, polyether block amides, polyether block ester copolymer, polyesters, fluoropolymers, polyvinyl chloride, thermoset silicone, latex, poly-isoprene rubbers, polyolefin, or other medical grade polymers, or combinations thereof, can also be utilized without departing from the scope of the subject disclosure.

Figure 2:
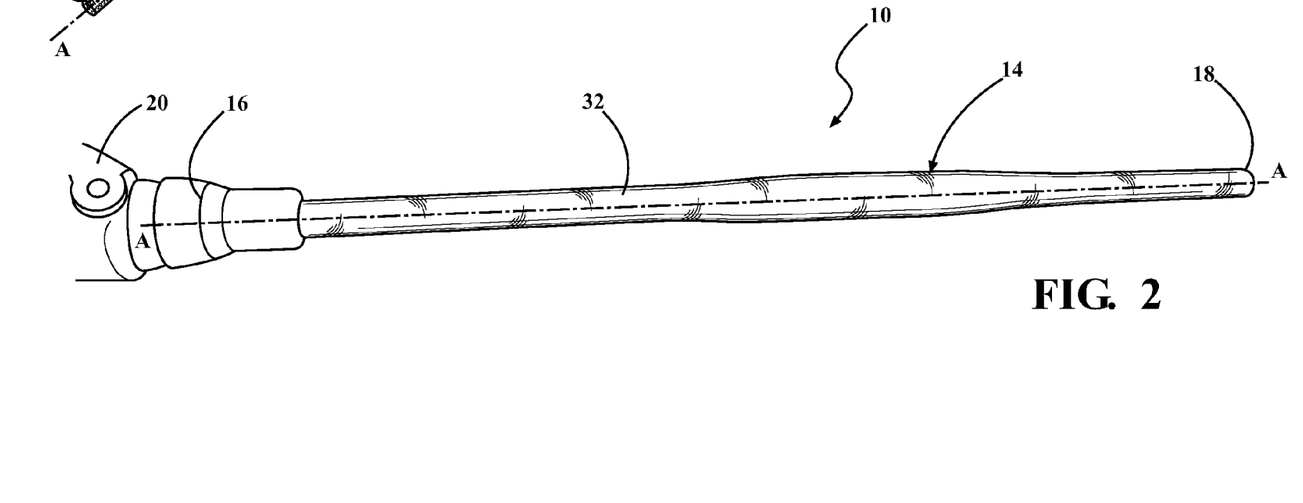
FIG. 2 is a perspective view of the expandable introducer sheath illustrating a protective sheath disposed in overlaying and surrounding relationship with the outer layer.

As best shown in FIG. 2, a protective sheath 32 can be disposed in overlaying and surrounding relationship with the outer layer 24 to provide a protective layer or barrier for the introducer sheath 10 when disposed within the body vessel. In a preferred embodiment, the protective sheath 32 is comprised of ePTFE to allow the protective sheath 32 to radially expand in conjunction with the outer layer 24 and the expandable reinforcement member 26 during axial movement of the medical device 12 through the introducer sheath 10. The ePTFE protective sheath 32 also adds lubricity and provides a low friction barrier for the introducer sheath that eases its insertion into the body vessel.

As best shown in FIGS. 3-6, in an embodiment, the outer layer 24 can be provided with at least cut or slit 34 which extends longitudinally and is disposed between the proximal and distal ends 16, 18 to facilitate radial expansion of the outer layer 24 relative to the axis A during axial movement of the medical device through the introducer sheath 10. For example, the outer layer 24 can be provided with a longitudinal cut or slit 34 which extends from the distal end 18 along a portion of the outer layer 24 and which is preferably aligned with an expansion area of the expandable reinforcement member 26. When a protective sheath 32 is disposed in overlaying relationship with the outer layer 24, the protective sheath 32 functions to cover the at least one cut or slit 34. As best shown in FIG. 4, in a preferred embodiment, the inner liner 22 can correspondingly include a fold 36 in an area which aligns with an expansion area of the expandable reinforcement member 26 as well as the at least one cut or slit 34 disposed in the outer layer 24. The fold 36 of the inner liner 22 facilitates radial expansion as a medical device 12 is axially advanced through the introducer sheath 10, and also allows for a reduced inner diameter of the inner layer 22.

Figures 7B, 7C:
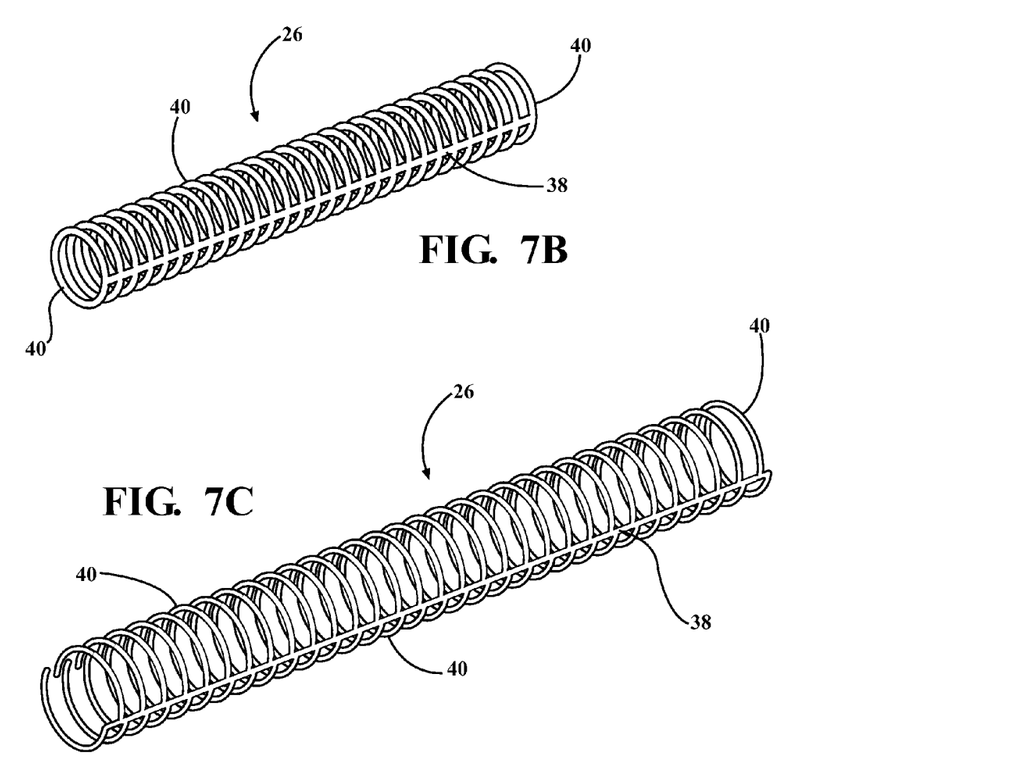
FIG. 7B is a perspective view of the first embodiment of the expandable reinforcement member in a contracted condition.
FIG. 7C is a perspective view of the first embodiment of the expandable reinforcement member in an expanded condition.

As best shown in FIGS. 7A-7C, in a first embodiment, the expandable reinforcement member 26 includes a spine 38 which extends between the proximal and distal ends 16, 18 and a plurality of ribs 40 which extend radially from the spine 38 and circumferentially about the axis A. In accordance with the above mentioned disclosure, the ribs 40 are radially expandable from a contracted position, shown in FIG. 7B, to an expanded position, shown in FIG. 7C, as the medical device 12 is introduced into the introducer sheath 10. As mentioned above, the expandable reinforcement member 26 is comprised of stainless steel, Nitinol, or the like and thus the ribs 40 are configured to return or spring back to the contracted position when the medical device 12 exits the introducer sheath 10 The spine 38 and ribs 40 of the expandable reinforcement member 26 are preferably fabricated by either laser cutting a tube or photoetching and rolling a flat pattern.

Figure 8A:
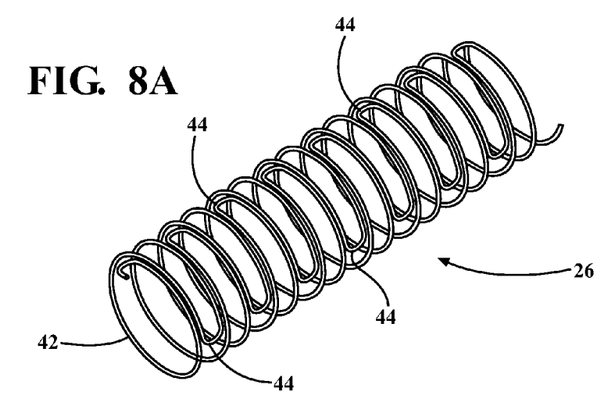
FIG. 8A is a perspective view illustrating a second embodiment of the expandable reinforcement member.
Figure 8B:
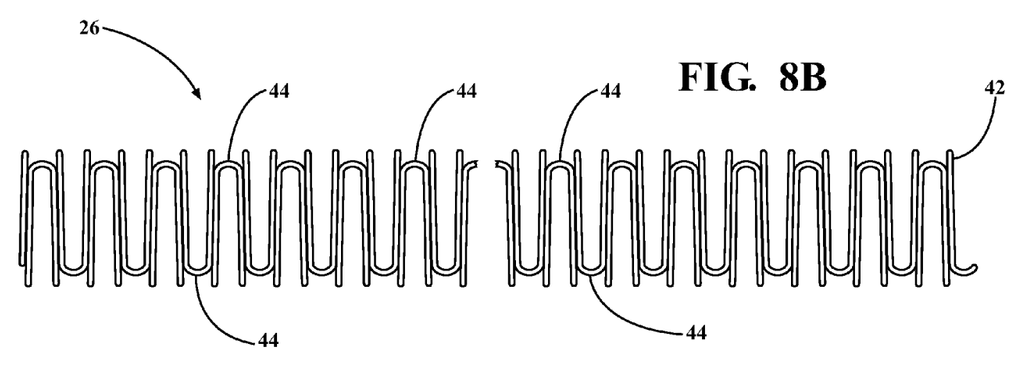
FIG. 8B is a top view of the second embodiment of the expandable reinforcement member.

As best shown in FIGS. 8A and 8B, in a second embodiment, the expandable reinforcement member 26 includes a single wire 42 which extends continuously between the proximal and distal ends 16, 18. The continuous, single wire 42 is wrapped or threaded to define a series of loops 44, with each of the loops 44 extending circumferentially about the axis A and interleaved between adjacent loops 44. In a preferred arrangement, adjacent loops 44 extend in opposite radially circumferential directions relative to one another to allow the adjacent loops 44 to slide relative to one another and effectuate an expansion of the reinforcement member 26 as the medical device 12 is introduced into the introducer sheath 10.

Figure 9:
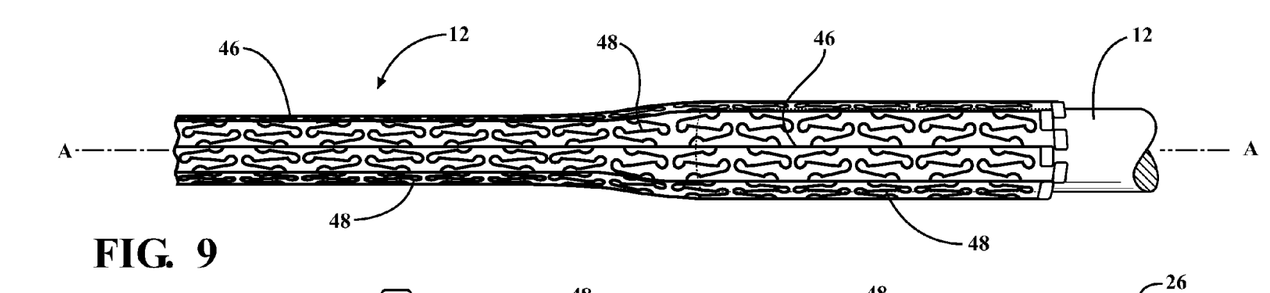
FIG. 9 is a perspective view of a third embodiment of the expandable reinforcement member.
Figure 10:
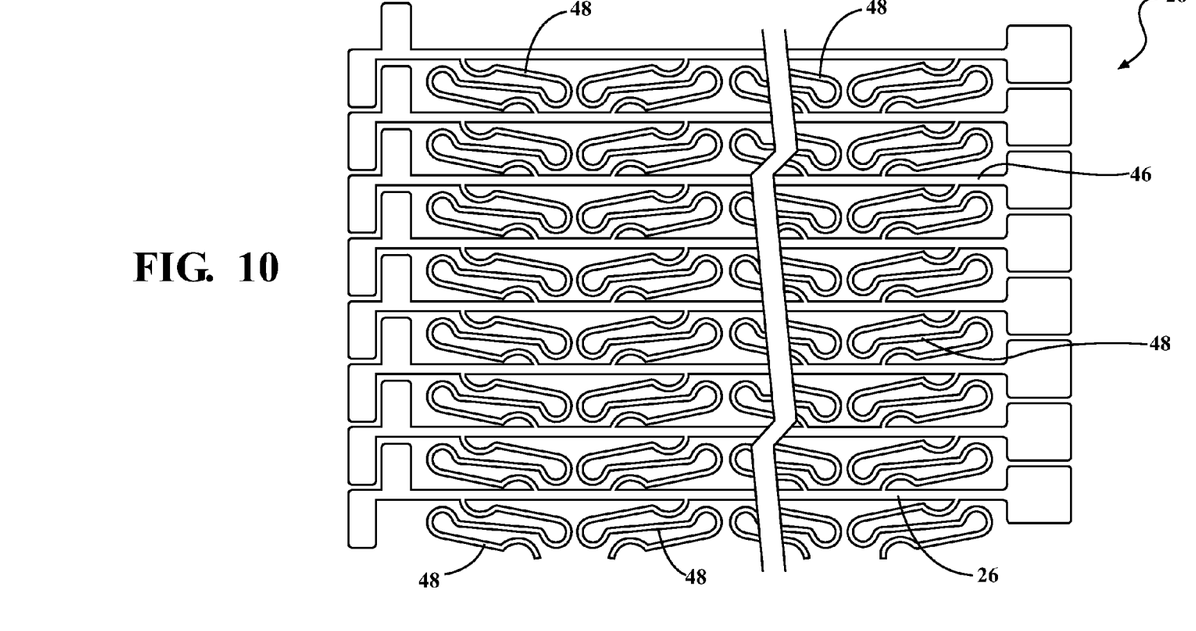
FIG. 10 is a magnified view of a portion of the third embodiment of the expandable reinforcement member.

As best shown in FIGS. 9 and 10, in a third embodiment, the expandable reinforcement member 26 includes a plurality of struts 46 disposed in spaced relationship to one another and each extending longitudinally between the proximal and distal ends 16, 18 in spaced and parallel relationship to the axis A. The expandable reinforcement member 26 also includes a plurality of linkages 48 each extending radially between adjacent struts 46, with each linkage 48 disposed in interleaved relationship with adjacent struts 46. As best shown in FIG. 9, each of the linkages 46 are radially expandable from their contracted or static position as a medical device 12 is introduced into the introducer sheath 10, and are configured to return or spring back to the contracted position when the medical device 12 exits the introducer sheath 10. In a preferred arrangement, the struts 346 and linkages 48 of the expandable reinforcement member 26 are preferably fabricated by laser cutting a tube.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. An expandable introducer sheath for use in inserting a medical device into a body vessel of a patient comprising:
    a body extending from a proximal end to a distal end along an axis A;
    said body including an inner layer, an outer layer, and an expandable reinforcement member disposed between said inner and outer layers;
    said expandable reinforcement member configured to radially expand as the medical device is axially advanced or retracted through the introducer sheath; and
    a protective sheath disposed in overlaying and surrounding relationship with said outer layer and radially expandable in conjunction with said outer layer and said expandable reinforcement member during axial movement of the medical device through the introducer sheath.

2. An expandable introducer sheath as set forth in claim 1, wherein said expandable reinforcement member includes a spine extending between said proximal and distal ends and a plurality of ribs extending radially from said spine and circumferentially about said axis A.

3. An expandable introducer sheath as set forth in claim 1, wherein said expandable reinforcement member includes a single wire which extends continuously between said proximal and distal ends.

4. An expandable introducer sheath as set forth in claim 3, wherein said single wire is wrapped to define a series of loops, with each of said loops in said series of loops extending circumferentially about said axis A and being interleaved between adjacent loops of said series of loops.

5. An expandable introducer sheath as set forth in claim 4, wherein said adjacent loops of said series of loops extend in opposite radial circumferential directions relative to one another for allowing said adjacent loops to slide relative to one another and effectuate radial expansion of said reinforcement member as the medical device is introduced into said introducer sheath.

6. An expandable introducer sheath as set forth in claim 1, wherein said expandable reinforcement member includes a plurality of struts disposed in spaced relationship to one another and each extending longitudinally between said proximal and distal ends and a plurality of linkages each extending radially between adjacent spines.

7. An expandable introducer sheath as set forth in claim 6, wherein said each of the linkages are radially expandable from their contracted or static position as a medical device is introduced into the introducer sheath, and are configured to return or spring back to the contracted position when the medical device exits the introducer sheath.

8. An expandable introducer sheath as set forth in claim 6, wherein said expandable reinforcement member is fabricated by laser cutting a tube.

9. An expandable introducer sheath as set forth in claim 1, wherein said expandable reinforcement member is comprised of a shape memory material to facilitate a return of said expandable reinforcement member to its unexpanded condition following an exit of the medical device from said introducer sheath.

10. An expandable introducer sheath as set forth in claim 9, wherein said expandable reinforcement member is comprised of Nitinol or stainless steel.

11. An expandable introducer sheath as set forth in claim 9, wherein said expandable reinforcement member is comprised of a rigid thermoplastic material.

12. An expandable introducer sheath as set forth in claim 1, wherein said inner layer is comprised of a lubricous, low friction polymeric material.

13. An expandable introducer sheath as set forth in claim 12, wherein said inner layer is comprised of expandable polytetrafluoroethylene (ePTFE).

14. An expandable introducer sheath as set forth in claim 1, wherein said outer layer is comprised of a thermoplastic material.

15. An expandable introducer sheath as set forth in claim 1, wherein said protective sheath is comprised of expandable polytetrafluoroethylene (ePTFE).

16. An expandable introducer sheath as set forth in claim 1, wherein said outer layer includes at least one slit which extends longitudinally and is disposed between said proximal and distal ends.

17. An expandable introducer sheath as set forth in claim 16, wherein said inner layer includes a fold disposed in aligned relationship with said at least one slit of said outer layer.

18. An expandable introducer sheath as set forth in claim 1, wherein said body includes an enlarged portion disposed adjacent said proximal end, said enlarged portion having a first diameter being complementary to the medical device.

19. An expandable introducer sheath as set forth in claim 18, wherein said body includes a tapered portion extending from said distal end to said enlarged portion, said tapered portion having a second diameter being smaller than said first diameter of said enlarged portion for providing a smaller profile of said introducer sheath to facilitate an initial insertion into the body vessel.

* * * * *